(12) United States Patent
Bang et al.

(10) Patent No.: US 7,276,049 B2
(45) Date of Patent: Oct. 2, 2007

(54) DISPOSABLE SAFETY SYRINGE

(76) Inventors: Sang Hyok Bang, 3rd Floor, 228-2 Jungja-dong, Boondang-gu Sungnam-City, Kyunggi-do 463-815 (KR); Young Ja Choi, 1805 Hyundai Panteon, 21-2, Soonae-dong, Boondang-gu Sungnam-City, Kyunggi-do 463-825 (KR)

( * ) Notice: Subject to any disclaimer, the term of this patent is extended or adjusted under 35 U.S.C. 154(b) by 461 days.

(21) Appl. No.: 10/830,889

(22) Filed: Apr. 23, 2004

(65) Prior Publication Data
US 2005/0049557 A1   Mar. 3, 2005

(30) Foreign Application Priority Data
Aug. 25, 2003   (KR) ................. 20-2003-0027183 U (51) Int. Cl.
*A61M 5/32* (2006.01)
*A61M 5/00* (2006.01)
(52) U.S. Cl. ..................... 604/198; 604/110
(58) Field of Classification Search ............. 604/110, 604/192–198, 263, 181, 187; 128/919
See application file for complete search history.

(56) References Cited
U.S. PATENT DOCUMENTS
6,419,658 B1 * 7/2002 Restelli et al. ............. 604/110

* cited by examiner

Primary Examiner—Matthew F. DeSanto
(74) Attorney, Agent, or Firm—Ladas & Parry LLP

(57) ABSTRACT

A disposable safety syringe designed to prevent syringe handlers from being pricked by a needle by covering the needle with a needle shield, is provided. Special attention should be given to syringe needles because they are sharp enough to cause needle stick injuries before and after use. In particular, if a user is accidentally injured by a blood-stained needle, serious infections might be caused through the needle. Accordingly, the needle is covered with the needle shield after use. The needle shield is fitted over a syringe cylinder. A stopping tab prevents the needle shield from sliding off the cylinder. Inserting tabs are formed by cutting part of shield walls, and locking grooves are formed in the end of the inserting tabs. A fixing adapter has an engagement sill formed in the inner side thereof and a number of elastic fins in the outer side thereof, which is fitted on the locking tab of the needle fixer.

3 Claims, 14 Drawing Sheets

DISPOSABLE SAFETY SYRINGE

This application claims priority under 35 U.S.C. 119 from Republic of Korea Patent Application No. KR20-2003-0027183, filed Aug. 25, 2003, the entire disclosure of which is incorporated herein by reference.

BACKGROUND OF THE INVENTION

1. Field of the Invention

The present invention relates to a disposable safety syringe designed to prevent syringe handlers from being pricked by a needle by covering the needle with a needle shield.

2. Description of the Related Art

Disposable safety syringes are widely used due to the concerns that infectious diseases such as hepatitis and AIDS virus may be transmitted to a third party via needles of used syringes. However, the needles should be handled with much care before and after use because they are very sharp.

In particular, blood-stained needles may cause infections or injuries to medical practitioners such as doctors and nurses, or a third party who are pricked by the needles due to careless handling.

Thus, it is required that a safety syringe that is used single-time and disposable safely. That is, it is required that the safety syringe is designed to prevent sharp needles from causing injuries to medical practitioners or a third party by covering the needles with needle shields.

The prior art inventions of the same inventor as that of this invention are Korea Utility Model Registration Nos. 254002 entitled "Disposable safety syringe," 195390 entitled "Safety syringe," and 166124 entitled "Safety syringe," and 245065 entitled "Disposable safety syringe."

SUMMARY OF THE INVENTION

To solve the above problems, it is an object of the present invention to provide a disposable safety syringe with a built-in needle shield which is installed in the outside of a syringe cylinder, and can be slidably moved over a needle, in which the needle shield is pushed forward over the needle and locked to protect the needle inside thereof after use.

It is another object of the present invention to provide a disposable safety syringe with a needle-protection shield which can remove the concerns that used needles may cause infections to medical parishioners such as doctors and nurses, and a third party, since special attention should be given to syringe needles because they are sharp enough to cause needle stick injuries, and in particular, if a user is accidentally injured by a blood-stained needle, serious infections might be caused through the needle.

According to an aspect of the present invention, there is provided a disposable safety syringe for use as a non-detachable disposable syringe having a built-in needle which is fixed inside a needle fixer at the distal end of a syringe cylinder or a detachable disposable syringe having a separate needle which should be assembled with a needle fixer, which has a plunder provided on the inner face of the syringe cylinder, the disposable safety syringe comprising: a locking tab formed at the needle fixer of both types of syringes; a cylinder-shaped movable needle shield which Is slidably moved along the cylinder and is fitted on the outer surface of the cylinder; a stopping tab which prevents the needle shield from sliding off the cylinder at the leading end of the needle shield; inserting tabs formed by cuffing part of shield walls at the rear end of the needle shield; locking grooves formed in the end of the inserting tabs; a number of front-end protrusions and a number of rear-end protrusions formed on the inner side of the needle shield; a cylinder grip formed in the rear end of the cylinder; holes formed on the inner face of the cylinder grip to lock with the inserting tabs of the rear end of the needle shield; and a fixing adapter having an engagement sill formed in the inner side thereof and a number of elastic fins in the outer side thereof, which is fitted on the locking tab of the needle fixer.

Preferably, on the inner face of the number of elastic fins of the fixing adapter which is fixedly engaged with the needle fixer is formed a cylinder-shaped wall on the inner circumferential surface of which a screw-shaped sills is formed to hold the syringe needle tight.

Preferably, on the inner face of the cylinder-shaped needle shield are formed a number of front protrusions and a number of rear protrusions whose cross-sectional shapes have both tilted sides and vertical sides.

BRIEF DESCRIPTION OF THE DRAWINGS

The above and other objects and advantages of the present invention will become more apparent by describing the preferred embodiment thereof in more detail with reference to the accompanying drawings in which.

DETAILED DESCRIPTION OF THE INVENTION

Hereinbelow, a disposable safety syringe according to preferred embodiments of the present invention will be described with reference to the accompanying drawings.

Figure 1:
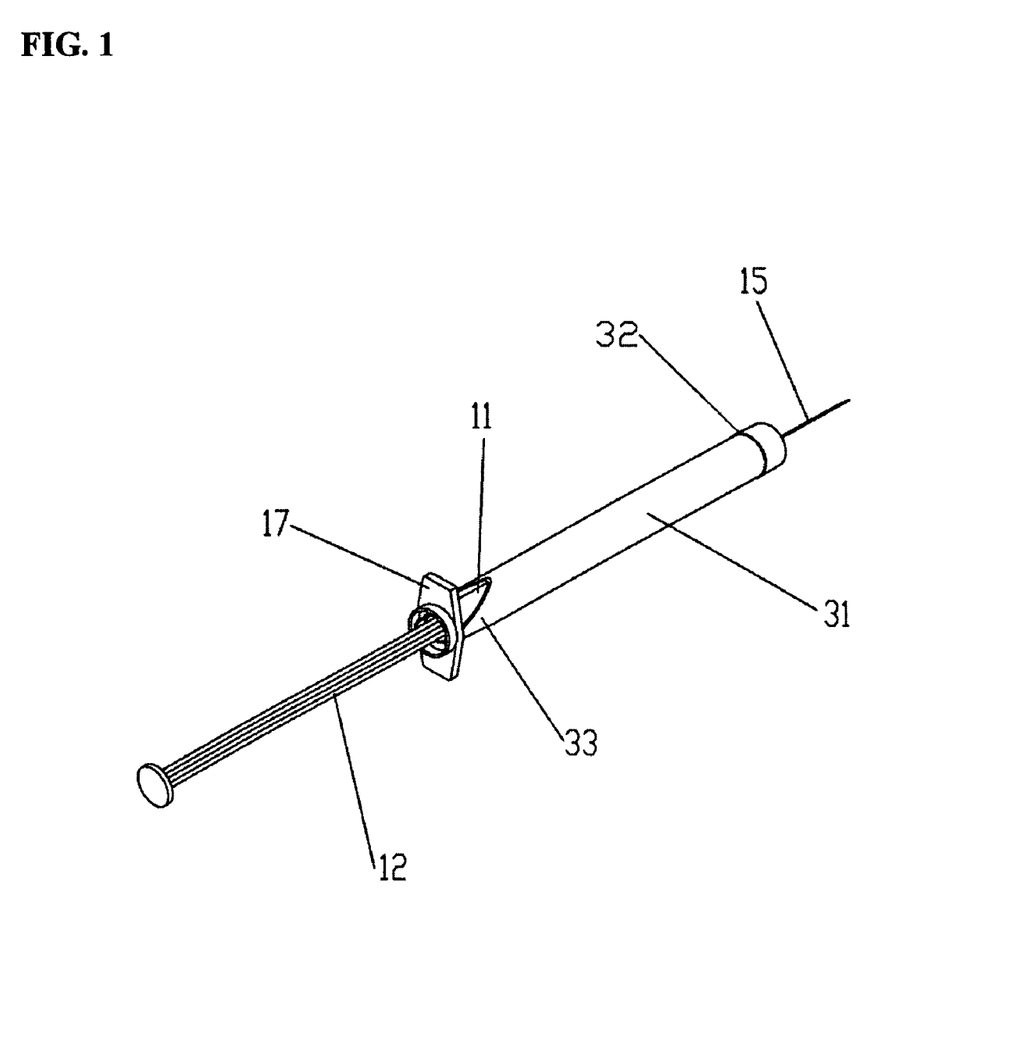
FIG. 1 is a perspective view of a disposable safety syringe according to the present invention immediately before use.
Figure 2:
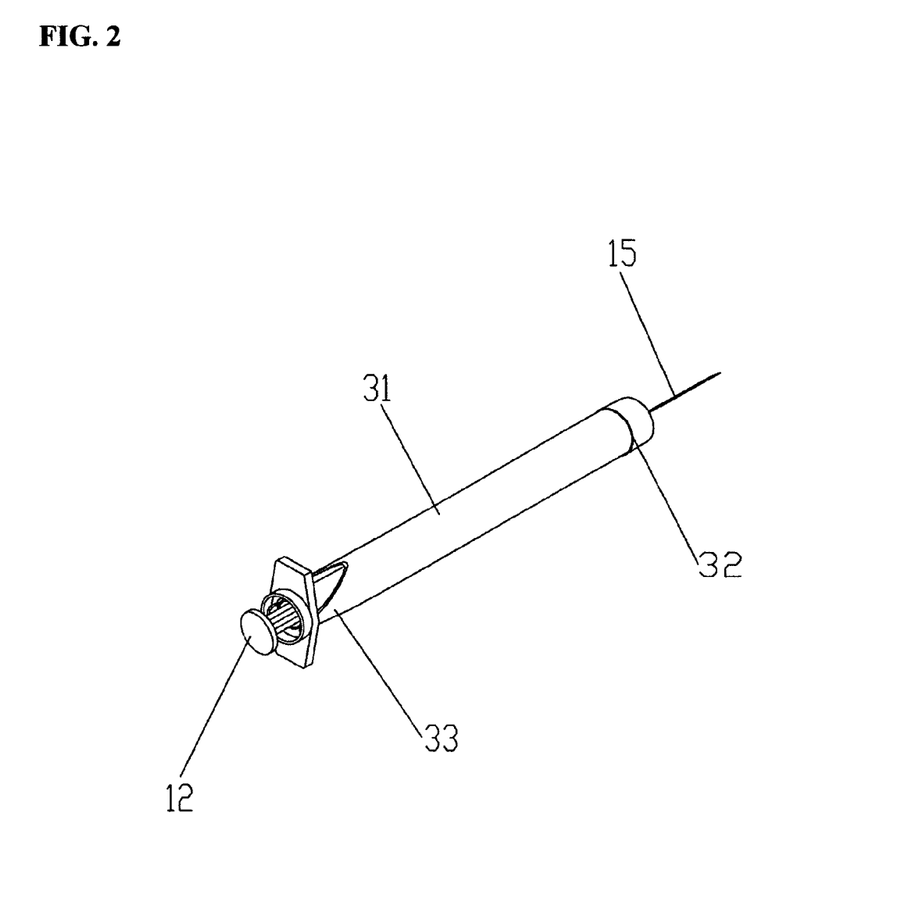
FIG. 2 is a perspective view of the disposable safety syringe of FIG. 1 immediately after use.
Figure 3:
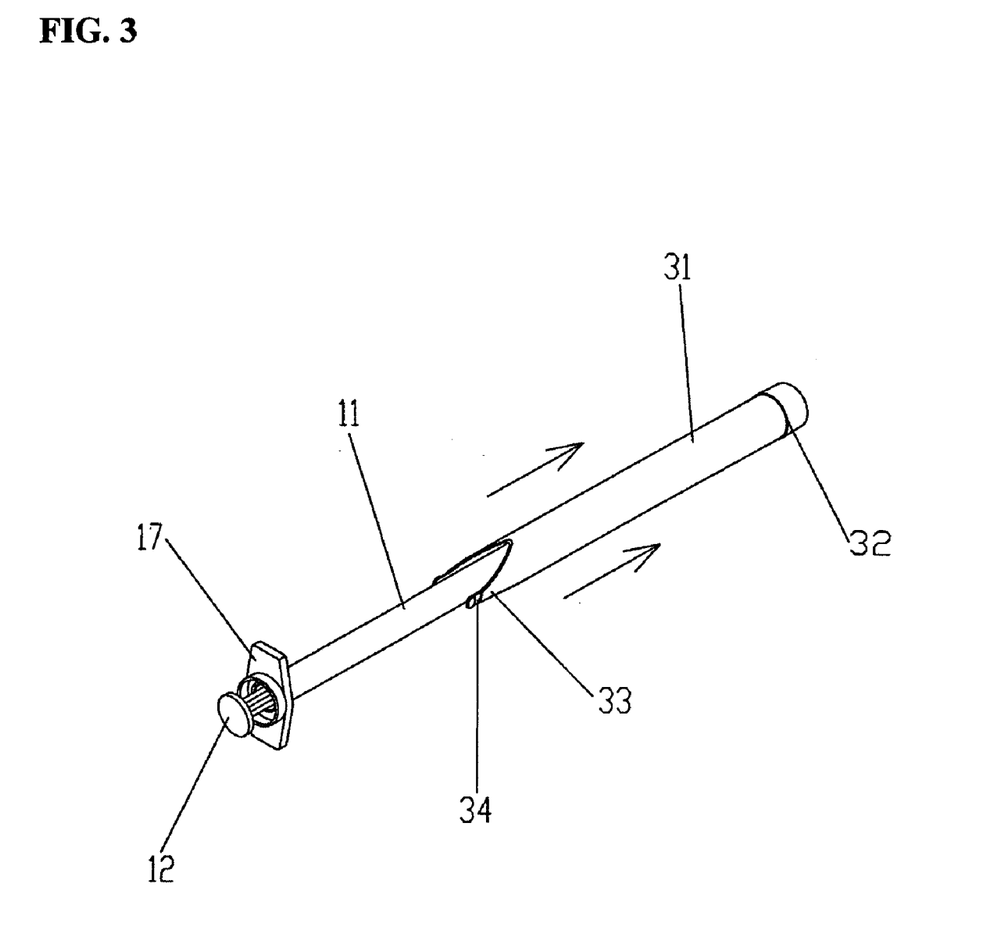
FIG. 3 is a perspective view of the disposable safety syringe whose needle shield is pushed forward to cover the needle of the disposable safety syringe after use.
Figure 4:
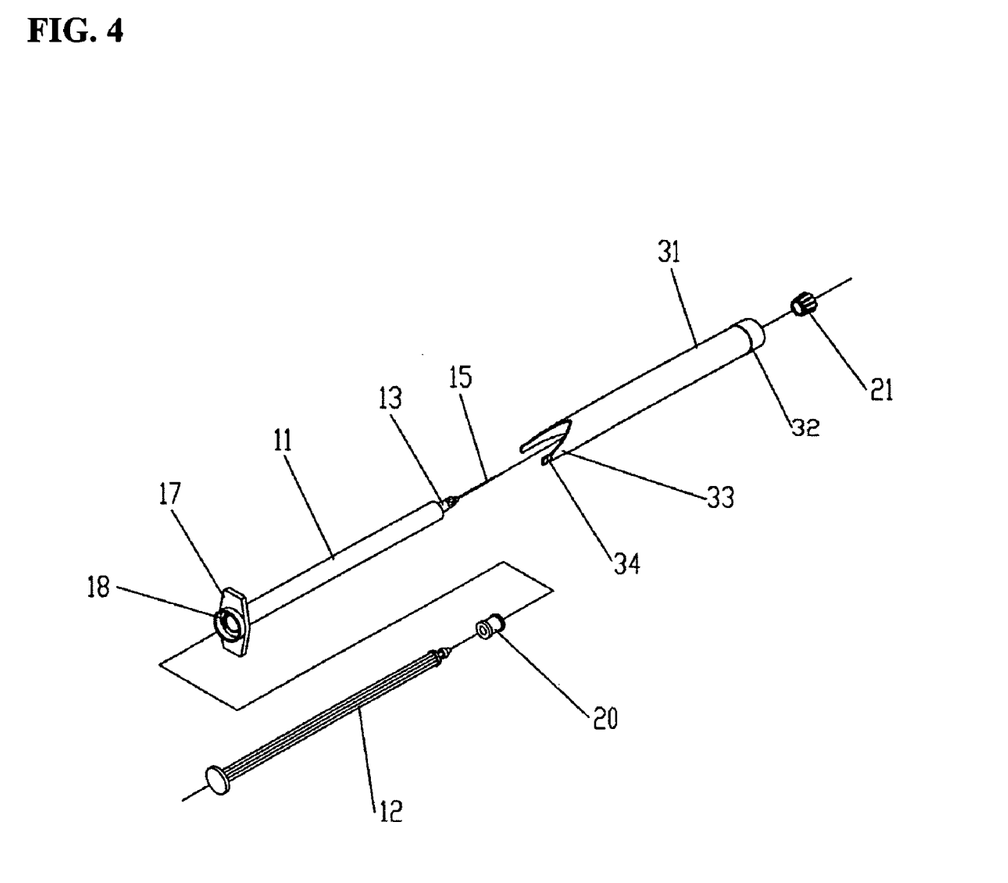
FIG. 4 is an exploded perspective view of the disposable safety syringe with a non-detachable needle.
Figure 5:
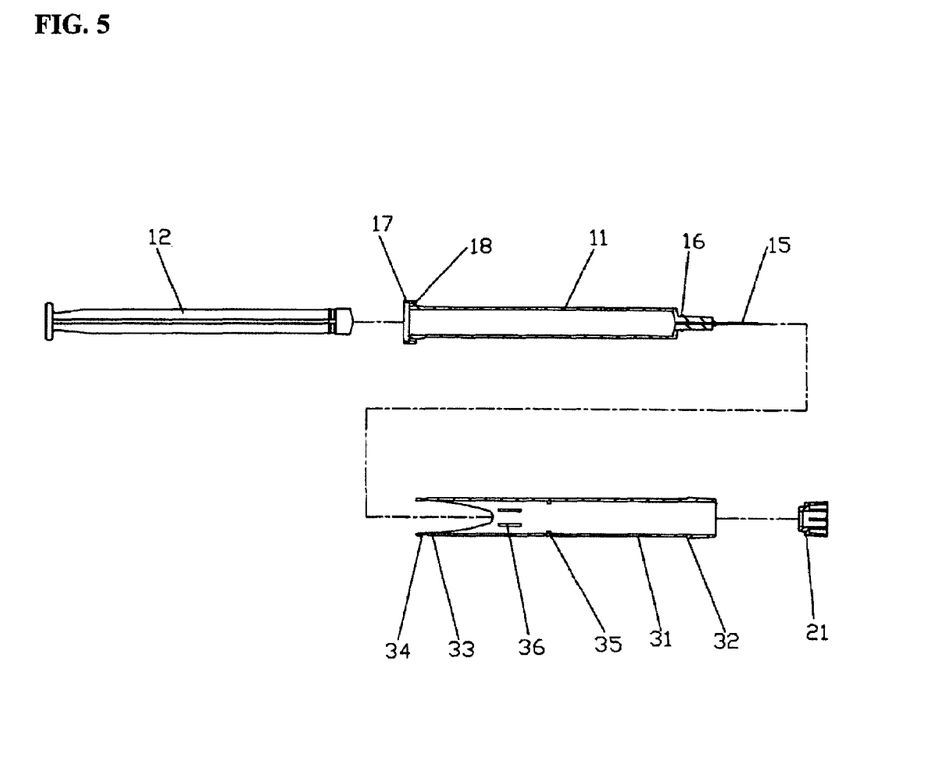
FIG. 5 is an exploded cross-sectional view of the disposable safety syringe with a non-detachable needle.
Figure 6:
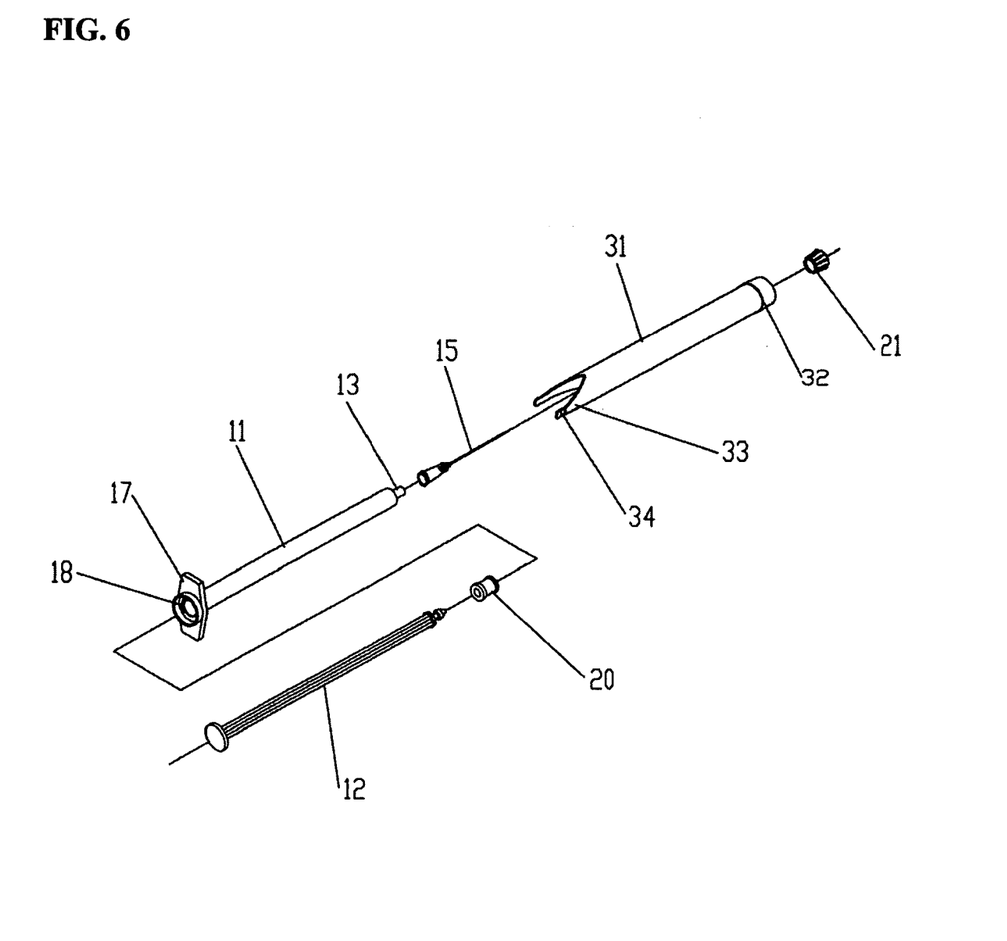
FIG. 6 is an exploded perspective view of the disposable safety syringe with a detachable needle.
Figure 7:
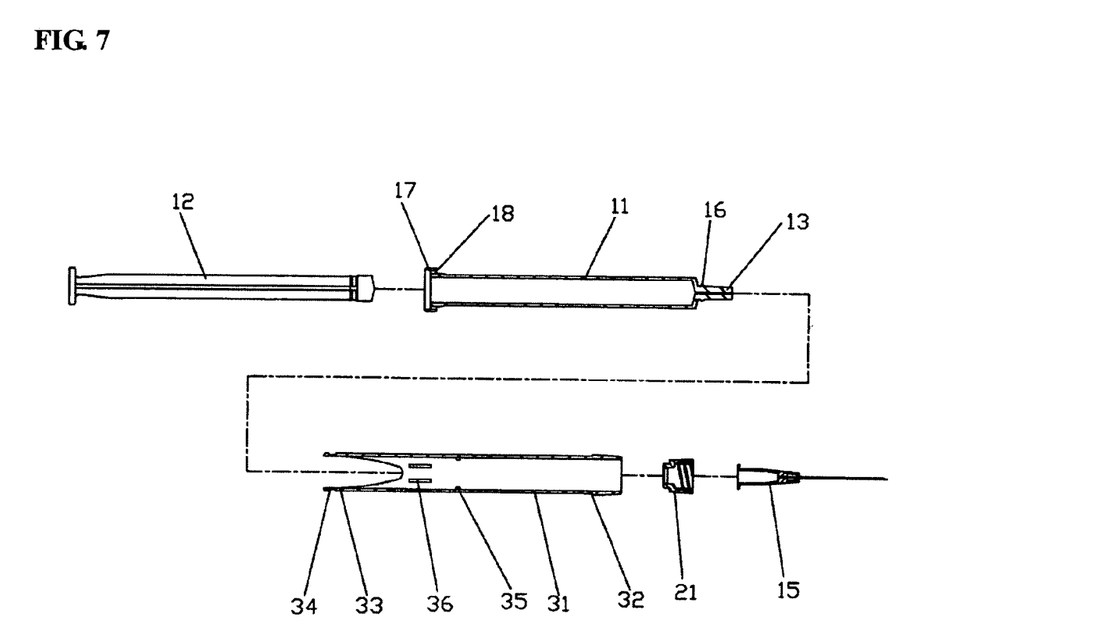
FIG. 7 is an exploded cross-sectional view of the disposable safety syringe with a detachable needle.
Figure 8:
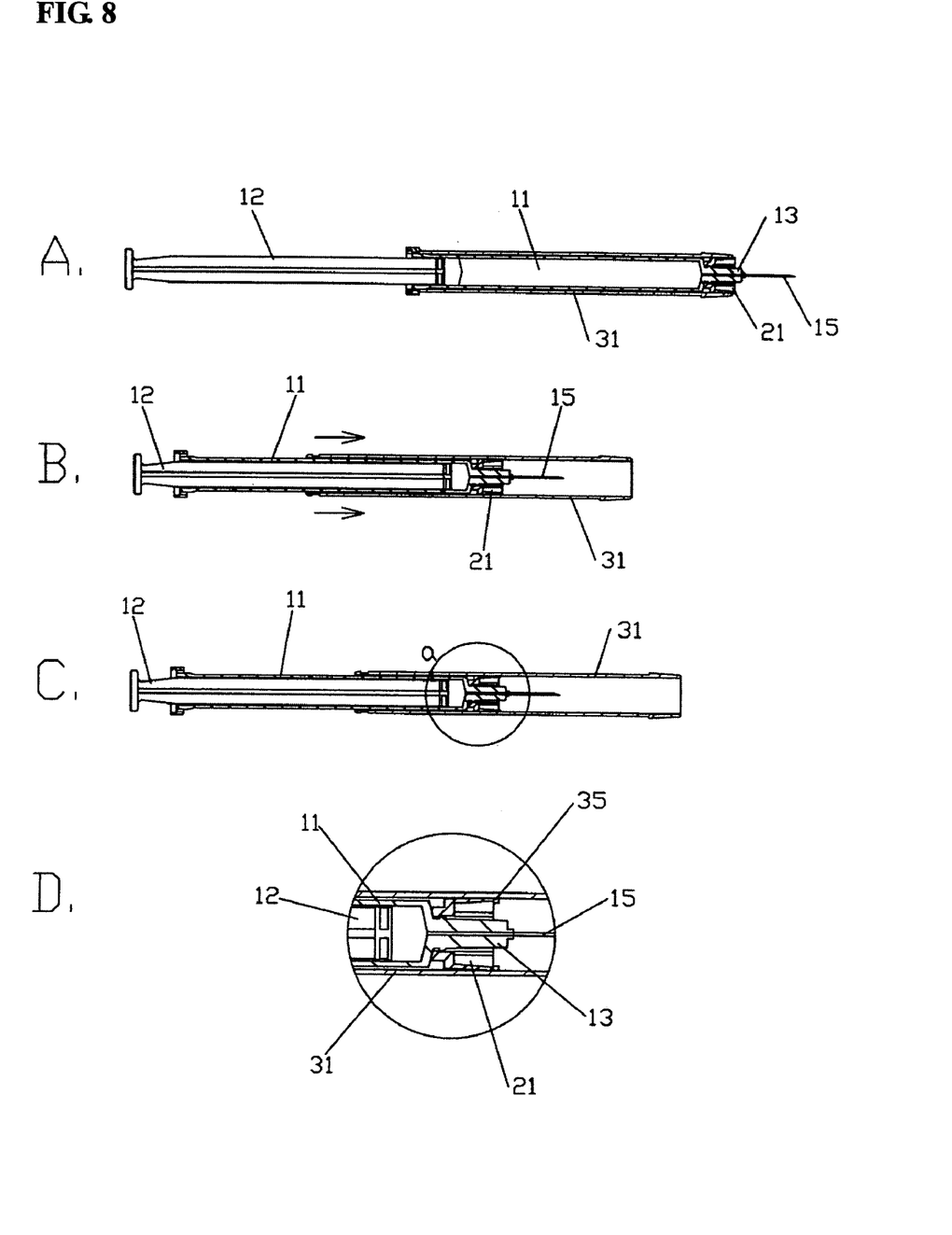
FIG. 8A is a cross-sectional view of the disposable safety syringe with a non-detachable needle before use.
FIG. 8B is a cross-sectional view of the disposable safety syringe with a non-detachable needle after use and with its needle shield being pushed forward.
FIG. 8C is a cross-sectional view of the disposable safety syringe with a non-detachable needle after use and with its protection shield being fixed.
FIG. 8D is an enlarged cross-sectional view of a portion "a" of FIG. 8C.
Figure 9:
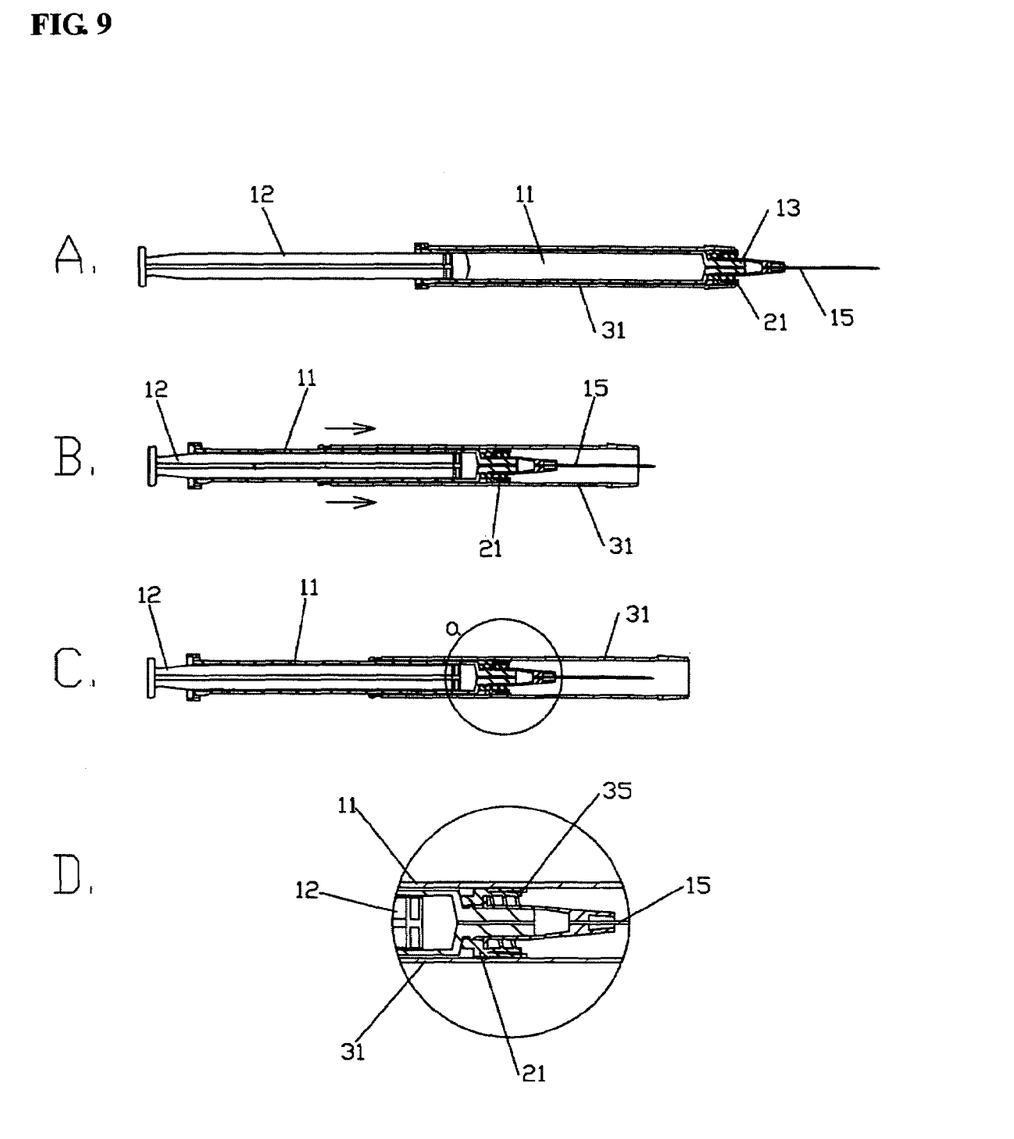
FIG. 9A is a cross-sectional view of the disposable safety syringe with a detachable needle before use.
FIG. 9B is a cross-sectional view of the disposable safety syringe with a detachable needle after use and with its protection shield being pushed forward.
FIG. 9C is a cross-sectional view of the disposable safety syringe with a detachable needle after use and with its protection shield being fixed.
FIG. 9D is an enlarged cross-sectional view of a portion "a" of FIG. 8C.
Figure 10:
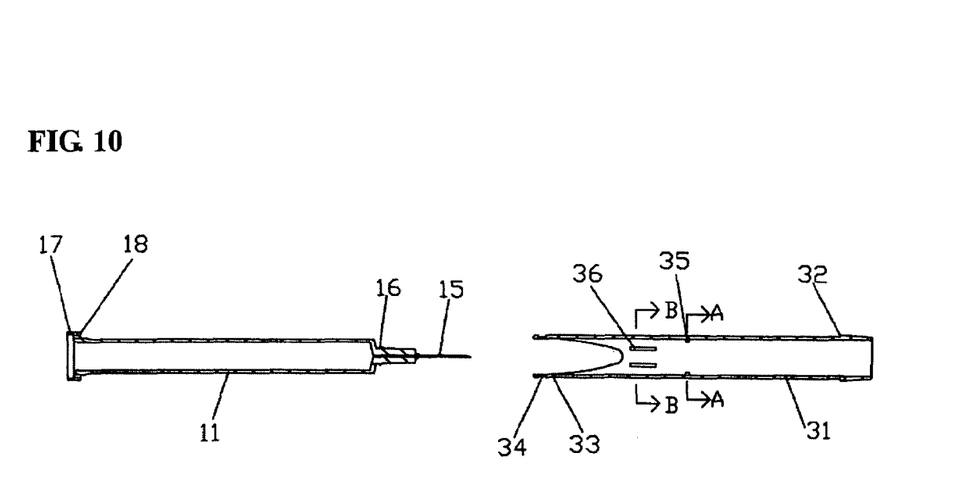
FIG. 10 is a perspective view of parts of the disposable safety syringe according to the present invention.
Figure 11:
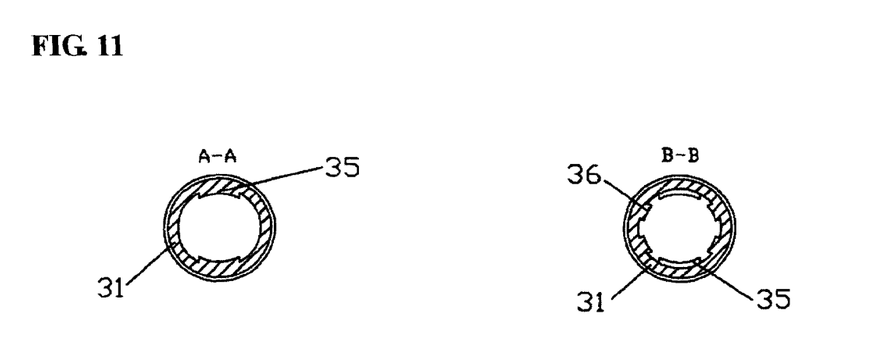
FIG. 11 is a respective cross-sectional view of an A-A line and a B-B line of FIG. 10.
Figure 12:
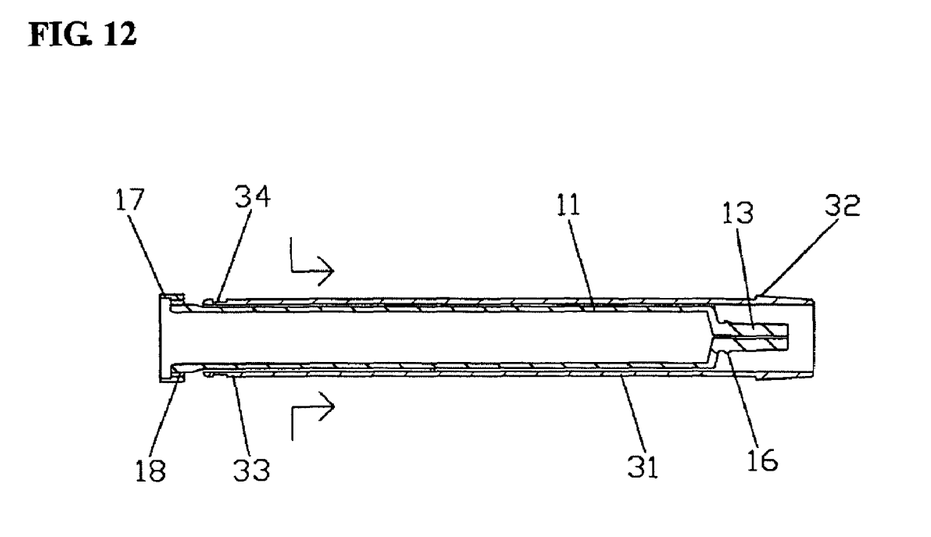
FIG. 12 is an enlarged cross-sectional view showing a connection state of joints of the disposable safety syringe.
Figure 13:
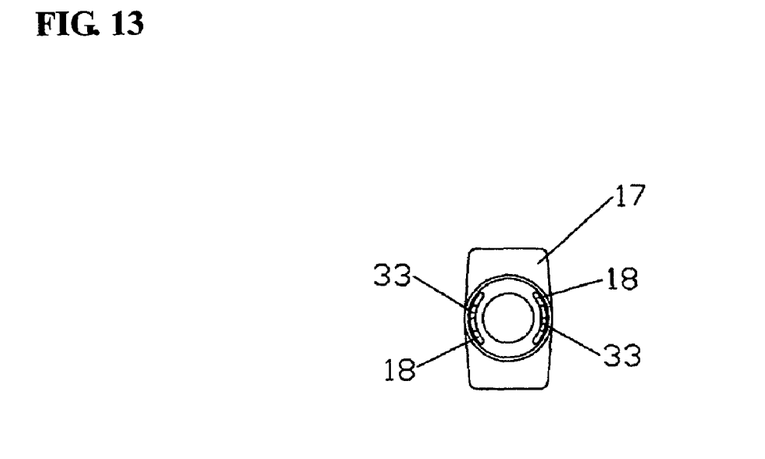
FIG. 13 is a lateral view of FIG. 12.
Figure 14:
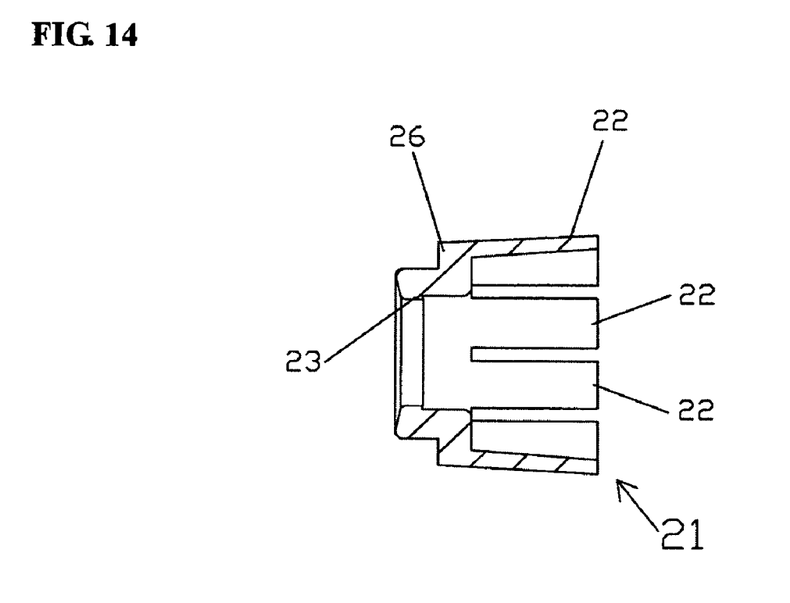
FIG. 14 is a cross-sectional view of a fixed adapter for use in the disposable safety syringe with a non-detachable deposable syringe.
Figure 15:
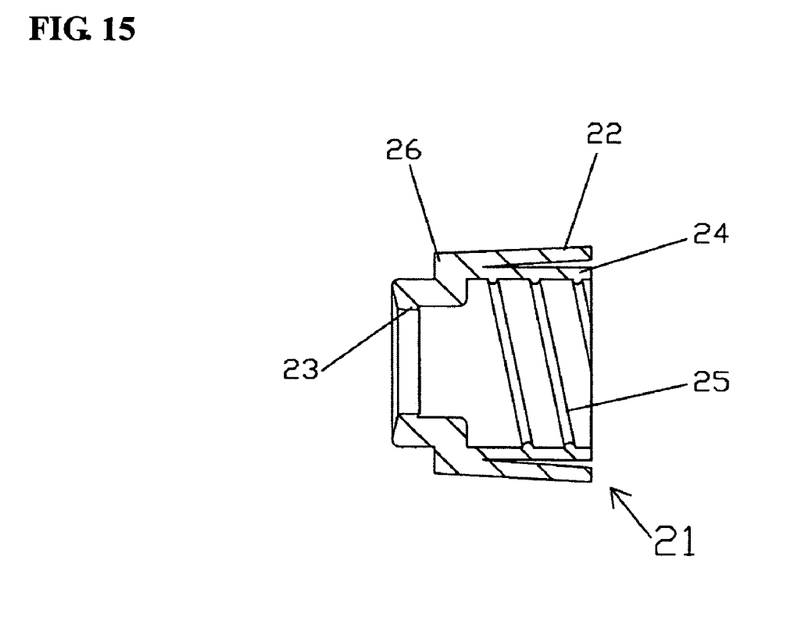
FIG. 15 is a cross-sectional view of a fixed adapter for the disposable safety syringe with a detachable deposable syringe.
Figure 16:
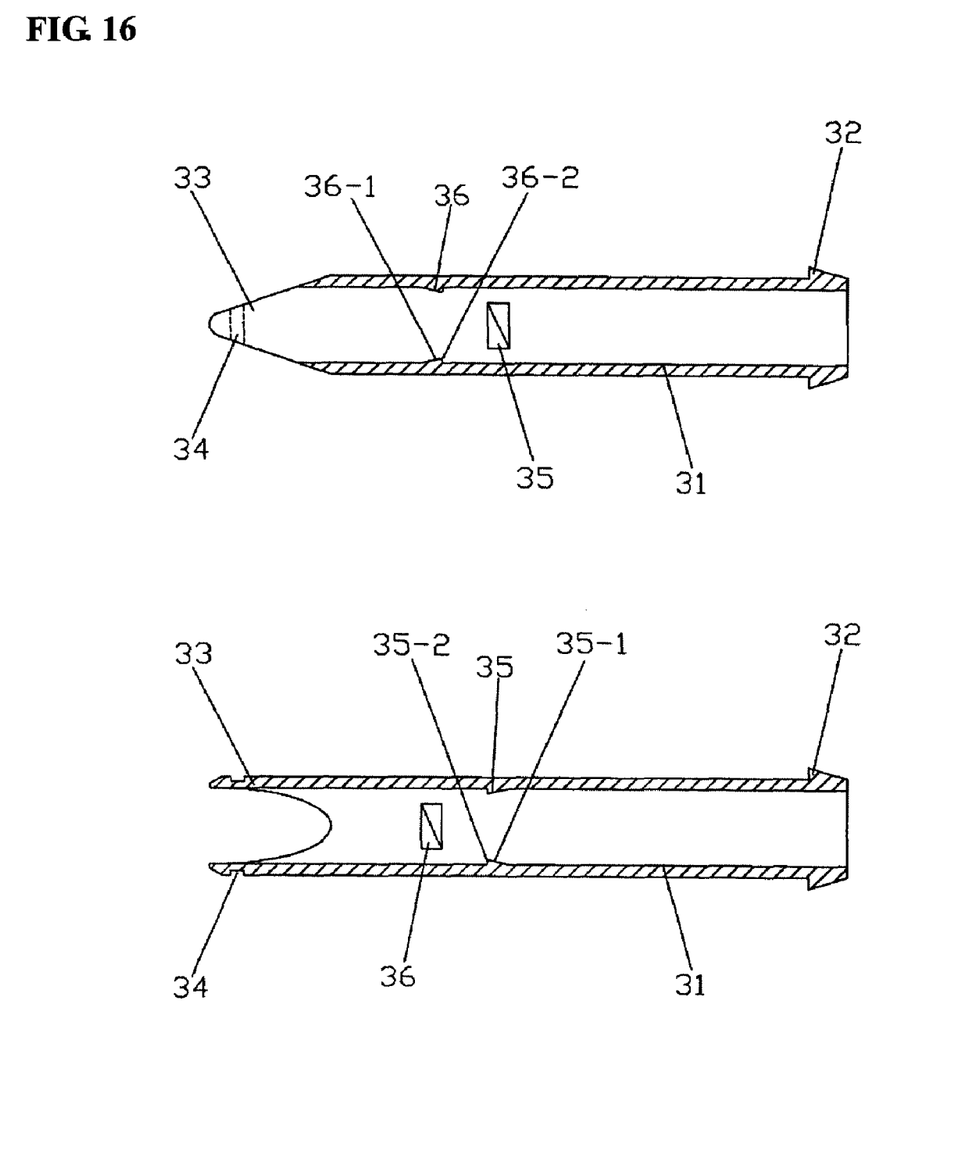
FIG. 16 is a crow-sectional view showing a needle shield for use in a disposable safety syringe according to another embodiment of the present invention.
Figure 17:
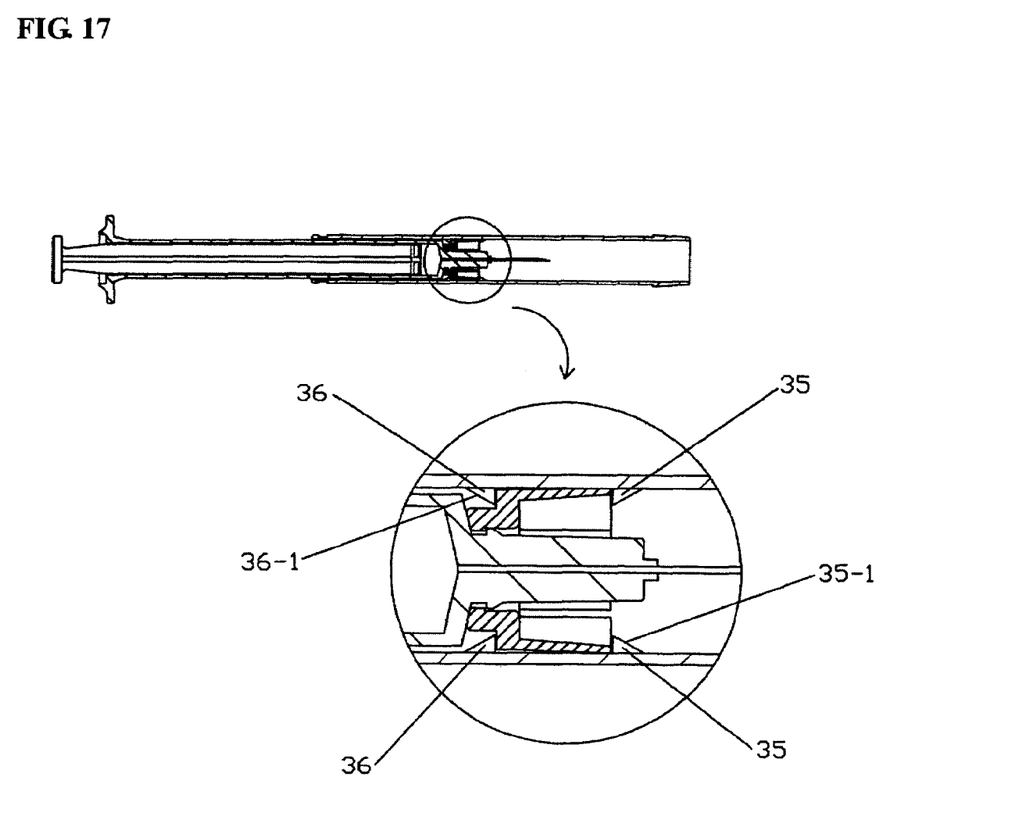
FIG. 17 is a cross-sectional view and partially enlarged view showing a needle shield for use in a disposable safety syringe according to still another embodiment of the present invention.

Referring to FIGS. 1 through 17, on the inner face of a syringe cylinder 11 is formed a plunder 12. Here, a non-detachable disposable syringe has a built-in needle which is fixed inside a needle fixer 13 at the distal end of the syringe cylinder 11. A detachable disposable syringe has a separate needle 15 which should be assembled with the needle fixer 13. Both types of syringes have locking tabs 16 at the needle fixer 13 of the syringes 11. A cylinder-shaped movable needle shield 31 is fitted over the cylinder 11 of the syringe. At the front end of the needle shield 31 is formed a stopping tab 32 which prevents the shield from sliding off the cylinder 11. Shield walls at the rear end of the needle shield 31 are cut to form front and rear inserting tabs 33.

At the outside of the inserting tabs 33 are formed locking grooves 34 and on the inner side of the needle shield 31 are formed a number of front-end protrusions 35 and a number of rear-end protrusions 36. At the rear end of the cylinder 11 has a cylinder grip 17 which has holes 18 on the inner face of the cylinder grip 17 to lock with inserting tabs 33 of the needle shield 31. A locking tab 16 of the needle fixer 13 is locked with an engagement sill 23 of a fixing adapter 21 when the locking tab 16 is inserted into the adapter 21.

On the inner face of the adapter 21 is formed the engagement sill 23 and at the outer face of the adapter 21 are formed a number of elastic fins 22, for example, 4 to 10 elastic fins. That is, the fixing adapter 21 having the engagement sills 23 inside and the number of elastic fins 22 outside, is pushed over the locking tabs 16 of the needle fixer 13 to be jointed with the locking tabs 16.

On the inner face of the number of elastic fins 22 of the fixing adapter 21 is formed a cylinder-shaped wall 24 which has a screw-shaped sills 25 to hold the syringe needle tightly.

On the inner face of the cylinder-shaped needle shield 31 are formed a number of front-end protrusions 35 and a number of rear-end protrusions 36 which have both tilted sides 35-1 and 36-1 and vertical sides 36-2 and 36-2.

A reference numeral 20 denotes a piston packing which is inserted into the plunger 12.

More detailed description of the present invention and its functions are as follows.

Most of the disposable syringes are categorized into two types. One is a disposable syringe with a non-detachable needle in a needle fixer 13 at the front end of a syringe cylinder 11. The other has a detachable needle 15 which should be assembled into a needle fixer 13 at the front end of a syringe cylinder 11 immediately before use.

Non-detachable needles are mostly used for small sized disposable syringes (less than 3 cc) and detachable types are for middle and large sized syringes.

For detachable syringes, needles are tapped into needle fixers at the front end of syringe cylinders or spun into screws of the needle fixers.

The present invention can be used with both non-detachable disposable syringes and detachable disposable syringes.

When a cylinder-shaped needle shield 31 is pushed in over a syringe cylinder 11, the locking grooves 34 of the inserting tabs 33 of the needle shield 31 are fixed into the inserting holes 18 on the inner face of the grip 17 formed in the rear end of the cylinder 11, and then the engagement sills 23 in the inner side of the fixing adapter 21 are engaged with the locking tabs 16 of the needle fixer 13 so that the fixing adapter 21 is fixedly engaged with the needle fixer 13.

This invention is to deliver fluids to a patient through the syringe needle 15 by pushing the plunder 12 into the syringe cylinder 11. After use, the cylinder-shaped needle shield 31 over the outer face of the cylinder 11 is pushed forward to cover the needle 15 and fixed to prevent needle stick injuries.

At the front end of the cylinder 11 is formed the needle fixer 13 which has the locking tab 16. The locking tab 16 is locked with the engagement sill 23 of the fixing adapter 21.

Since the engagement sill 23 of the fixing adapter 21 and the locking tab 16 of the needle fixer 13 are firmly engaged with each other, it is not so easy to detach the adapter 21 from the needle fixer 13 after being locked.

The fixing adapter 21 has a number of elastic fins 22, for example, elastic fins 22 of 4~10 pieces and stopping tabs 26 at the rear ends of the number of elastic fins 22.

On the inner sides of the number of elastic fins 22 of the fixing adapter 21 is formed a cylinder-shaped wall 24. On the inner circumferential surface of the wall 24 are formed screws 25 to hold the syringe needle 15 tightly. A needle 15 of a detachable disposable syringe is spun along the screws 15 on the inner face of the cylinder-shaped wall 24 of the fixing adapter 21 into the needle fixer 13. Otherwise, the needle 15 is tapped in to the needle fixer 13, in order to be fixedly engaged with each other.

The cylinder-shaped needle shield 31 is slidably movable over the syringe cylinder 11. The rear-end wall of the needle shield 31 is cut to have two inserting tabs 33 each at the end of which has a locking groove 34. The locking grooves 34 are locked with the inserting holes 18 on the inner face of the grip 17 of the syringe cylinder 11. By depressing the inserting tabs 33, the locking grooves 34 are detached from the inserting holes 18 of the syringe cylinder grip 17. Thus, if a user pushes forward the needle shield 31 (toward the needle) while pushing down the inserting tab 33, the needle shield 31 is moved forward over the syringe needle 15.

The needle shield 31 which moves toward the needle 15 is pushed forward until the front-end protrusions 35 on the inner face of the shield 31 meet stopping sills 26 at the rear end of the fixing adapter 21. Then, if the needle shield 31 is pushed forward with a small amount of force, the front-end protrusions 35 meet the front ends of the number of elastic fins 22 of the fixing adapter 21. When the rear-end protrusions 36 of the shield 31 meet the stopping sills 26 at the rear end of the elastic fins 22, the needle shield 31 is fixedly secured so that it is not moved forward and backward any more.

That is, the needle shield 31 moves forward and fixedly stopped until the fixing adapter 21 is securely locked between the front-end protrusions 35 and the rear-end protrusions 36.

In other words, the shield 31 should be pushed forward over the syringe cylinder 11 until the elastic fins 22 of the fixing adapter 21 which is fixed with the needle fixer 13 are locked between the front-end protrusions 35 and the rear-end protrusions 36 on the inner face of the needle shield 31. If the needle shield 31 is firmly fitted, the needle 15 is covered with the needle shield 31 to prevent needle stick injuries.

INDUSTRIAL APPLICABILITY

Special attention should be given to sharp needles before and after use because the needles maybe contaminated by a patient's blood which can carry infectious diseases to the others who were accidentally injured by the needles.

Thus, the present invention provides a disposable safety syringe having an effect of preventing needle stick injuries with a needle shield which is released from a syringe cylinder before use and pushed forward over the syringe cylinder after use, until the needle shield securely covers the used needle, to thereby prevent any infections from contaminating medical practitioners such as doctors and nurses, and a third party, through the used needles.

What is claimed is:

1. A disposable safety syringe for use as a non-detachable disposable syringe having a built-in needle which is fixed inside a needle fixer at the distal end of a syringe cylinder or a detachable disposable syringe having a separate needle which should be assembled with a needle fixer, which has a plunger provided on the inner face of the syringe cylinder, the disposable safety syringe comprising:
   a locking tab formed at the needle fixer of both types of syringes;
   a cylinder-shaped movable needle shield which is slidably moved along the cylinder and is fitted on the outer surface of the cylinder;
   a stopping tab which prevents the needle shield from sliding off the cylinder at the leading end of the needle shield;
   inserting tabs formed by cuffing part of shield walls at the rear end of the needle shield;
   locking grooves formed in the end of the inserting tabs;
   a number of front-end protrusions and a number of rear-end protrusions formed on the inner side of the needle shield;
   a cylinder grip formed in the rear end of the cylinder;
   holes formed on the inner face of the cylinder grip to lock with the inserting tabs of the rear end of the needle shield; and
   a fixing adapter having an engagement sill formed in the inner side thereof and a number of elastic fins in the outer side thereof, which is fitted on the locking tab of the needle fixer.

2. A disposable safety syringe of claim 1, wherein, a cylinder-shaped wall on the inner circumferential surface of which a screw-shaped sills is formed to hold the syringe needle tight is formed on the inner face of the number of elastic fins of the fixing adapter which is fixedly engaged with the needle fixer.

3. A disposable safety syringe of claim 1, wherein, on the inner face of the syringe cylinder-shaped movable needle shield are formed a number of front protrusions and a number of rear protrusions whose cross-sectional shapes have both tilted sides and vertical sides.

* * * * *